United States Patent
Zhao et al.

(10) Patent No.: US 9,879,374 B2
(45) Date of Patent: Jan. 30, 2018

(54) STEAM IRON FOR RECEIVING A FRAGRANCE CARTRIDGE

(71) Applicant: KONINKLIJKE PHILIPS N.V., Eindhoven (NL)

(72) Inventors: Lihong Zhao, Eindhoven (NL); Yile Liao, Eindhoven (NL); Yong Jiang, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/306,582

(22) PCT Filed: Feb. 8, 2016

(86) PCT No.: PCT/EP2016/052608
§ 371 (c)(1),
(2) Date: Oct. 25, 2016

(87) PCT Pub. No.: WO2016/128347
PCT Pub. Date: Aug. 18, 2016

(65) Prior Publication Data
US 2017/0342652 A1    Nov. 30, 2017

(30) Foreign Application Priority Data

Feb. 10, 2015 (EP) ..................... 15154426

(51) Int. Cl.
*D06F 75/20* (2006.01)
*D06F 75/38* (2006.01)
*A61L 9/02* (2006.01)

(52) U.S. Cl.
CPC .............. *D06F 75/20* (2013.01); *D06F 75/38* (2013.01); *A61L 9/02* (2013.01)

(58) Field of Classification Search
CPC .......... D06F 75/10–75/26; D06F 75/36; D06F 75/38; D06C 7/00; A61L 9/02
See application file for complete search history.

(56) References Cited

U.S. PATENT DOCUMENTS

| 477,660 | A | * | 6/1892 | Hunter | .................... D06F 75/38 38/81 |
| 2,495,397 | A | * | 1/1950 | Weber | .................... D06F 75/12 38/77.6 |

(Continued)

FOREIGN PATENT DOCUMENTS

| DE | 29601699 U1 | 7/1997 |
| EP | 1582620 A1 | 10/2005 |

(Continued)

*Primary Examiner* — Ismael Izaguirre

(57) ABSTRACT

The present application relates to steam iron (1). The steam iron (1) comprises a sole plate (3). The sole plate (3) has a steam channel (6) for the passage of steam, an ironing surface (10), vents (4) for the passage of steam between the steam channel (6) and the ironing surface (10), an aperture (9) extending between the steam channel (6) and the ironing surface (10), and a fragrance cartridge (7) being received in the aperture (9) such that it extends into the steam channel (6) to diffuse fragrance in the steam channel (6). The aperture (9) secures the fragrance cartridge (10) in the sole plate (3) such that fragrance cartridge (7) is flush with the ironing surface (10). The present invention also relates to a fragrance cartridge (7) and to a method of imparting a fragrance to steam produced by a steam iron (1).

13 Claims, 3 Drawing Sheets

(56) References Cited

U.S. PATENT DOCUMENTS

| | | | | |
|---|---|---|---|---|
| 4,240,217 | A * | 12/1980 | Schwob | D06F 75/18 38/77.83 |
| 4,642,922 | A * | 2/1987 | Prudenziati | D06F 75/20 38/81 |
| 5,642,578 | A | 7/1997 | Hazan et al. | |
| 6,163,990 | A * | 12/2000 | Urata | D06F 75/14 38/77.8 |
| 6,351,901 | B1 * | 3/2002 | Amsel | D06F 75/14 38/77.8 |
| 7,661,212 | B2 * | 2/2010 | Hahn | D06F 75/10 210/282 |
| 2004/0096369 | A1 * | 5/2004 | Daoting | A61L 2/20 422/124 |
| 2010/0101122 | A1 * | 4/2010 | Nathamuni Balaji | D06M 23/02 38/97 |
| 2010/0213278 | A1 | 8/2010 | Zan | |

FOREIGN PATENT DOCUMENTS

| | | |
|---|---|---|
| GB | 2304740 A | 3/1997 |
| JP | 07699 A | 1/1995 |
| JP | 3057428 U | 7/1998 |
| JP | 2007061448 A | 3/2007 |

\* cited by examiner

STEAM IRON FOR RECEIVING A FRAGRANCE CARTRIDGE

This application is the U.S. National Phase application under 35 U.S.C. §371 of International Application No. PCT/EP2016/052608, filed on Feb. 8, 2016, which claims the benefit of International Application No. 15154426.9 filed on Feb. 10, 2015. These applications are hereby incorporated by reference herein.

FIELD OF THE INVENTION

The present invention relates to a steam iron for receiving a fragrance cartridge, and a fragrance cartridge for such a steam iron. The present invention also relates to a method of imparting a fragrance to steam intended to be sprayed over garments during ironing by a steam iron.

BACKGROUND OF THE INVENTION

It is known that ironing a fragrance into a garment will result in the fragrance being released from the garment for an extended period of time. For example, the garment can be pre-sprayed with a liquid fragrance prior to ironing. However, pre-spraying the garment is time consuming and may result in the liquid fragrance staining the garment.

Fragrance may also be imparted to the garment by pouring drops of a fragranced essential oil into the water tank of the steam iron. Therefore, when the steam iron is operated, the liquid water in the water tank is evaporated and is imparted with the fragrance of the essential oil. However, it is difficult for the user to judge how much essential oil should be added to the water tank. Furthermore, the essential oil in the water tank does not evaporate with the water and so most of the essential oil remains in the water tank and thus the steam does not have a strong fragrance. Additionally, the water tank needs to be completely emptied of liquid water and essential oil before a different fragrance is used.

U.S. Pat. No. 6,351,901 discloses a steam iron with a steam generating device for generating steam and an application device for releasing additives to the steam. The application device consists of a capillary device for the release of additive to the steam.

SUMMARY OF THE INVENTION

It is an object of the invention to provide a steam iron and a method of imparting a fragrance to steam produced by a steam iron which substantially alleviates or overcomes the problems mentioned above.

According to the present invention, there is provided a steam iron comprising a sole plate, said sole plate comprising a steam channel for the passage of steam, an ironing surface, vents for the passage of steam between the steam channel and the ironing surface, an aperture extending between the steam channel and the ironing surface, and a fragrance cartridge being received in said aperture such that it extends into the steam channel to diffuse fragrance in the steam channel, wherein the aperture secures the fragrance cartridge in the sole plate such that the fragrance cartridge is flush with the ironing surface.

In use, the user may supply fragrance to the fragrance cartridge. Upon operation of the steam iron, steam flows along the steam channel and is fluidly communicated with the fragrance cartridge. This causes the fragrance that is absorbed in the fragrance cartridge to be released into the steam in the steam channel, which is then vented onto the article to be steamed to impart the fragrance thereto. Therefore, the user is able to easily and reliably impart fragrance to the article to be steamed without having to pre-spray the article with fragrance or supply fragrance to the water tank of the steam iron. In addition, since the fragrance cartridge is received in the sole plate, which is heated, heat from the sole plate will encourage evaporation of the fragrance from the fragrance cartridge such that more fragrance is imparted to the steam in the steam channel. Furthermore, the fragrance cartridge being located in the sole plate provides the advantage that the user is easily able to access the fragrance cartridge when the steam iron is located on its base. Therefore, replenishing the amount of fragrance in the fragrance cartridge is simplified.

In use, the user may supply fragrance to the fragrance cartridge. Upon operation of the steam iron, steam flows along the steam channel and is fluidly communicated with the fragrance cartridge such that fragrance is imparted to the steam which is then vented onto the article to be steamed. Therefore, the user is able to easily and reliably impart fragrance to the article to be steamed without having to pre-spray the article with fragrance or supply fragrance to the water tank of the steam iron. In addition, since the fragrance cartridge is received in the sole plate, which is heated, heat from the sole plate will encourage evaporation of the fragrance from the fragrance cartridge such that more fragrance is imparted to the steam in the steam. Furthermore, the user is able to easily access the fragrance cartridge when the steam iron is located on its base. Therefore, replenishing the amount of fragrance in the fragrance cartridge is simplified.

The aperture may be circular with a diameter of between 5 mm-10 mm. The aperture may comprise a screw thread adapted to cooperate with a screw thread formed in the fragrance cartridge.

The aperture may extend between the steam channel and the ironing surface in the proximity of where steam enters the steam channel. This allows for the steam to have a fragrance imparted to it when it enters the steam channel such that there is more time for the fragrance to be spread evenly throughout the steam before the steam exits the sole plate via the vents.

The fragrance cartridge may comprise a fragrance receiving element and a holder to hold said fragrance receiving element.

In one embodiment, the fragrance receiving element extends through the holder from the steam channel to enable it to be filled with liquid fragrance without removing the holder from the aperture. This allows for easy refilling of the fragrance cartridge since the user is able to supply fragrance to the porous fragrance receiving element without first having to remove the holder from the sole plate.

In one embodiment, the holder comprises a recess to receive the fragrance receiving element and wherein the recess only extends partially through the holder such that the fragrance receiving element extends partially through the holder and is inaccessible from the ironing surface when the fragrance cartridge is received in the aperture. Therefore, the holder forms a barrier between the flavour receiving element and the article to be steamed such that direct contact is prevented. Therefore, the chance of fragrance being leaked onto the article to be steamed is reduced.

The fragrance receiving element may be adapted to protrude into the steam channel. This increases the surface area of the fragrance receiving element that is in contact with the steam in the steam channel so that the amount of fragrance imparted to the steam is increased.

The fragrance receiving element may be made from a porous material.

In one embodiment, the holder lies flush with the ironing surface. Therefore, the holder is prevented from snagging on the article to be steamed when the ironing surface is moved over the surface of the article to be ironed.

In one embodiment, the holder is removably secured within the aperture in the sole plate. Therefore, the fragrance receiving element can easily be replaced if faulty or substituted with a fragrance receiving element that is imparted with a different fragrance.

The holder may be manually removable from the sole plate by movement of the holder relative to the sole plate. Therefore, the user can remove the holder to supply fragrance to the fragrance receiving element and can easily repair and/or replace the holder and fragrance receiving element.

The holder may be manually removable from the sole plate without use of a separate tool. This allows for the user to easily remove the holder to replace the fragrance receiving element or to supply fragrance thereto.

According to another aspect of the invention, there is provided a method of imparting a fragrance to steam intended to be sprayed over garments during ironing by a steam iron having a sole plate, said sole plate comprising a steam channel for the passage of steam, an ironing surface, vents for the passage of steam between the steam channel and the ironing surface, and an aperture extending between the steam channel and the ironing surface, the method comprising the steps of: disposing a fragrance cartridge in said aperture such that it extends into the steam channel to diffuse fragrance in the steam channel and is flush with the ironing surface; and, passing steam into the steam channel.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION OF THE EMBODIMENTS

Figure 1:
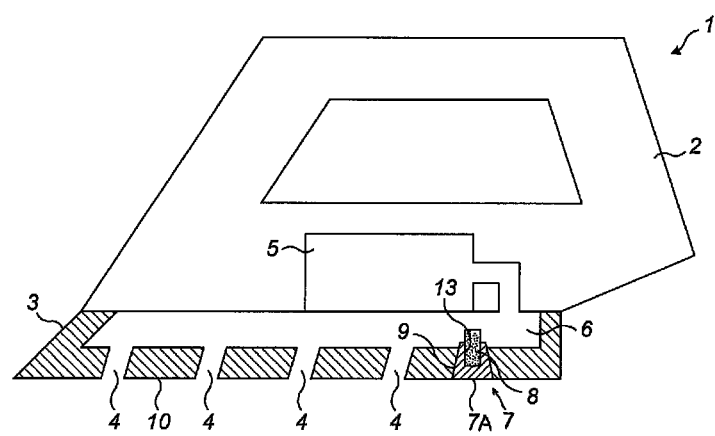
FIG. 1 is a schematic cross-sectional side view of a steam iron according to an embodiment of the invention.
Figure 2:
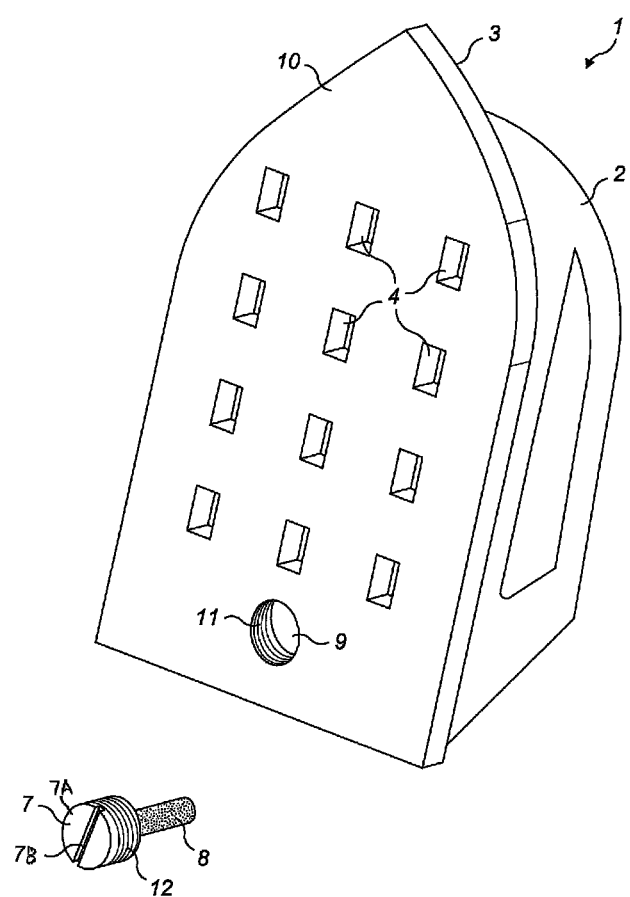
FIG. 2 is a perspective view of the steam iron of FIG. 1, with a holder removed from a sole plate of the steam iron.

Referring now to FIGS. 1 and 2, a steam iron 1 according to an embodiment of the invention is shown. The steam iron 1 comprises a body 2 and a sole plate 3. The steam iron 1 is configured to apply steam to an article to be ironed, such as a garment, through a plurality of steam vents 4 in the sole plate 3.

The steam iron 1 includes a steam generator 5 for generating steam. The steam generator 5 is of a conventional arrangement known to a person skilled in the art, for example comprising a pump (not shown) that supplies liquid water from a water tank (not shown) to a boiler (not shown). The boiler is configured to heat water within the boiler to make steam.

A steam channel 6 fluidly communicates the steam generator 5 with the plurality of steam vents 4 in the sole plate 3. Therefore, steam is able to flow from the steam generator 5, along the steam channel 6, and out of the steam vents 4 to act on the garment to be steamed.

The steam iron 1 further comprises a fragrance cartridge 7. The fragrance cartridge 7 comprises a holder 7A and a fragrance receiving element 8. The holder 7A comprises a recess 13 that is configured to receive the fragrance receiving element 8 such that an end of the fragrance receiving element 8 is securely contained in the holder 7A.

The sole plate 3 comprises an aperture 9 that extends through the thickness of the sole plate 3. The aperture 9 is configured to receive the holder 7A. The aperture 9 comprises a screw thread 11 that is configured to engage with a screw thread 12 of the holder 7A such that the fragrance cartridge 7 can be removably screwed into the aperture 9 of the sole plate 3.

The aperture 9 is circular and has a diameter of between 5-10 mm and the holder 7A is circular and has a corresponding diameter to fit snugly into the aperture 9. However, it will be recognised that in alternate embodiments the aperture 9 and holder 7A may be another shape and/or size.

The fragrance receiving element 8 may comprise a porous material. In the present embodiment, the porous material comprises foam. However, it should be recognised that the fragrance receiving element 8 may comprise a different porous material for example, cork or fabric.

In use, the user supplies a few drops of liquid fragrance to the fragrance receiving element 8. The porous material of the fragrance receiving element 8 absorbs the drops of liquid fragrance. The fragrance cartridge 7 is then screwed into the aperture 9. The fragrance may comprise, for example, an essential oil or perfume.

The sole plate 3 comprises a contact surface 10 that abuts the garment to be steamed. When the fragrance cartridge 7 is screwed into the aperture 9 in the sole plate 3, the holder 7A does not extend past the contact surface 10 and instead a surface of the holder 7A sits flush to the contact surface 10. This configuration prevents the holder 7A from snagging on the garment being steamed when the contact surface 10 of the sole plate 3 is moved over the surface of the garment to be steamed.

An end of the fragrance receiving element 8 extends into the steam channel 6 when the fragrance cartridge 7 is screwed into the aperture 9 of the sole plate 3. Therefore, upon operation of the steam generator 5, steam flows along the steam channel 6 and is fluidly communicated with the fragrance receiving element 8. This causes the fragrance that is absorbed in the fragrance receiving element 8 to be released into the steam in the steam channel 6. The steam is then vented through the plurality of steam vents 4 and onto the garment to be steamed such that the fragrance is imparted onto the garment.

The fragrance cartridge 7 can be unscrewed from the aperture 9 in the sole plate 3 to allow the user to access the fragrance receiving element 8. Therefore, the user can easily replenish the amount of fragrance absorbed in the fragrance receiving element 8. In addition, the fragrance receiving element 8 can be substituted with another fragrance receiving element (now shown) that is used to absorb a different fragrance. Therefore, mixing of different fragrances is prevented and there is no need for all of the fragrance in the fragrance receiving element 8 to be depleted before a different fragrance is used.

The fragrance cartridge 7 can easily be manually unscrewed from the aperture 9 without the need for a separate tool. The holder 7A comprises a slot 7B that is on the opposite side of the holder 7A to the fragrance receiving element 8. The slot 7B is accessible by the user when the holder 7A is received in the aperture 9 in the sole plate 3. Therefore, a user can insert their fingernail into the slot 7B to unscrew the holder 7A to remove the fragrance cartridge 7 from the aperture 9. In an alternate embodiment (not shown), the slot 7B is omitted and is replaced with one or more projections that can be gripped by the user to unscrew the holder.

Figure 3:
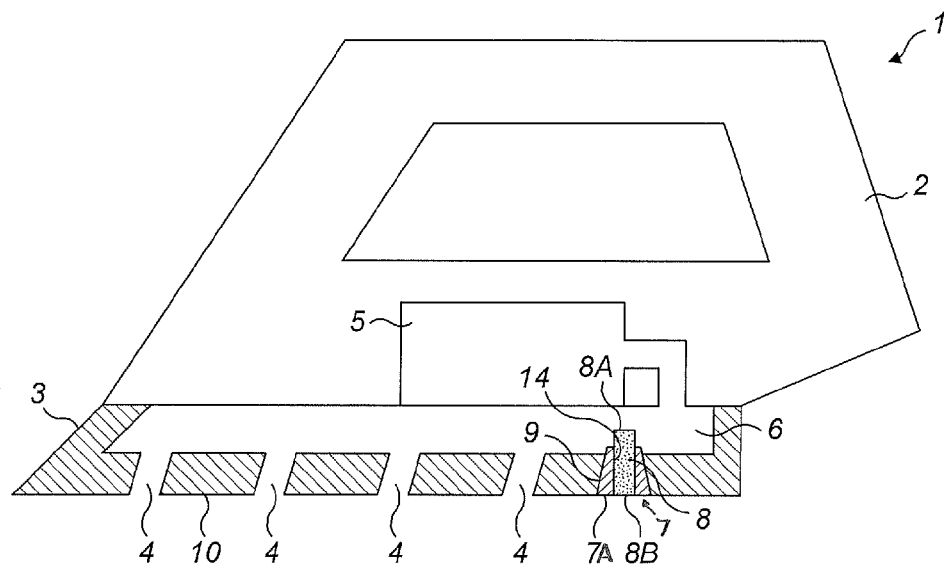
FIG. 3 is a schematic cross-sectional side view of a steam iron according to an alternative embodiment of the invention; and, FIG. 4 is a schematic cross-sectional side view of a steam iron according to an alternative embodiment of the invention.

Referring now to FIG. 3, a steam iron 1 according to an alternative embodiment of the invention is shown. The steam iron 1 comprises a body 2, sole plate 3, steam generator 5 and steam channel 6 that are similar to those described above in relation to FIGS. 1 and 2, with like features retaining the same reference numerals. A difference is that the steam iron 1 shown in FIG. 3 comprises a fragrance cartridge 7 that has a holder 7A with a passage 14 extending through the entire thickness of the holder 7A. The passage 14 extends from the steam channel 6 to the contact surface 10 of the sole plate 3.

The fragrance receiving element 8 is securely received in the passage 14 and extends from the steam channel 6 to the contact surface 10 of the sole plate 3. A first end 8A of the fragrance receiving element 8 extends into the steam channel 6 when the holder 7A is screwed into the aperture 9 of the sole plate 3 to impart fragrance to the steam in the steam channel 6. The distal second end 8B of the fragrance receiving element 8 does not protrude from the contact surface 10 of the sole plate 3 and, preferably, is flush with the contact surface 10. This prevents the holder 7A and the second end 8B of the fragrance receiving element 8 from snagging on the garment being steamed when the sole plate 3 is moved over the surface of the garment.

The user is able to supply drops of liquid fragrance to the fragrance receiving element 8 without first having to remove the fragrance cartridge 7 from the aperture 9 in the sole plate 3. This is because the second end 8B of the fragrance receiving element 8 sits flush to the contact surface 10 of the sole plate 3 and so the user is easily able to access the fragrance receiving element 8 to supply fragrance thereto. Thus, the user can replenish the fragrance absorbed in the fragrance receiving element 8 simply by orientating the steam iron 1 such that the sole plate 3 faces upwardly and then supply drops of liquid fragrance onto the exposed second end 8B of the fragrance receiving element 8.

The porous material of the fragrance receiving element 8 facilitates a capillary action which causes the fragrance to move along the fragrance receiving element 8 from the second end 8B to the first end 8A thereof. The first end 8A of the fragrance receiving element 8 protrudes into the steam channel 6. Therefore, drops of fragrance that are supplied to the second end 8B of the fragrance receiving element 8 travel along the fragrance receiving element 8 to be fluidly communicated with the steam in the steam channel 6 to impart a fragrance thereto.

In the embodiments described above, the user is able to unscrew the holder 7A from the aperture 9 in the sole plate 3 to remove the fragrance receiving element 8 from the fragrance cartridge 7. Therefore, the fragrance receiving element 8 can easily be replaced if it is broken, or swapped with an alternative fragrance receiving element that is imparted with a different fragrance.

Figure 4:
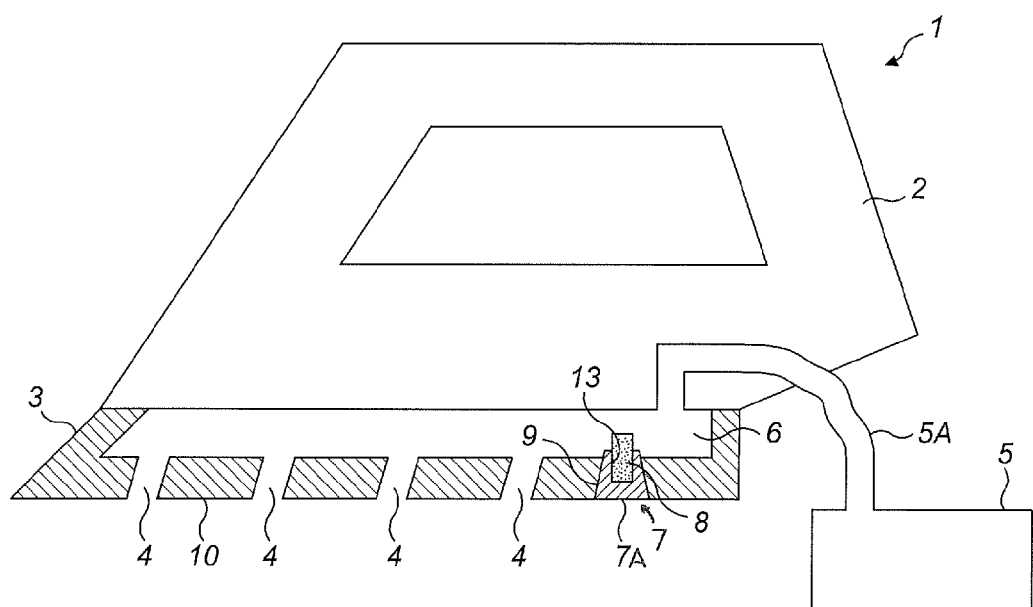

Referring now to FIG. 4, a steam iron 1 according to an alternative embodiment of the invention is shown. The steam iron 1 is similar to those described above in relation to FIGS. 1 to 3, with like features retaining the same reference numerals. A difference is that the steam iron 1 shown in FIG. 4 comprises a steam generator 5 that is located outside of the body 2 of the steam iron 1. A flexible hose 5A fluidly communicates the steam generator 5 with the steam channel 6. In use, steam is supplied from the steam generator 5 to the steam channel 6 via the flexible hose 5A and is imparted with a fragrance in the manner described above.

In the above described embodiments the aperture 9 and the holder 7A each comprise a screw thread 11, 12 to allow the holder 7A to be screwed into the aperture 9 such that the fragrance cartridge 7 is releasably secured to the sole plate 3. However, in alternate embodiments (not shown) the screw threads 11, 12 are omitted and instead the fragrance cartridge 7 is releasably secured in the aperture 9 in a different manner. For example, the holder 7A may be releasably clipped into the aperture 9 in the sole plate 3 or releasably secured therein by non-permanent adhesive.

In the above described embodiments the fragrance cartridge 7 is removable from the aperture 9 is the sole plate 3 to allow for easy replacement of the fragrance receiving element 8 and supply of the fragrance receiving element 8 with fragrance. However, in an alternate embodiment (now shown) the fragrance cartridge 7 is permanently fixed in the aperture 9 of the sole plate 3. For example, the holder 7A may be adhered to the sole plate 3 by permanent adhesive.

Although in the above described embodiments the fragrance receiving element 8 is removable from the holder 7A, to allow for easy maintenance and for the fragrance receiving element 8 to be swapped with another that is used to absorb a different fragrance, in alternate embodiments (not shown) the fragrance receiving element is permanently secured to the holder.

In the above described embodiments the user supplies drops of liquefied fragrance, for example perfume or essential oils, to the fragrance receiving element 8. However, it should be recognised that the fragrance receiving element 8 could alternatively be sprayed with a gaseous fragrance or provided with a solid fragrance, for example powdered fragrance. In another embodiment (not shown), the fragrance receiving element is pre-supplied with a fragrance such that the user does not have to apply fragrance to the fragrance receiving element and instead merely has to secure the fragrance receiving element to the sole plate using the holder.

The above embodiments as described are only illustrative, and not intended to limit the technique approaches of the present invention. Although the present invention is described in details referring to the preferable embodiments, those skilled in the art will understand that the technique approaches of the present invention can be modified or equally displaced without departing from the spirit and scope of the technique approaches of the present invention, which will also fall into the protective scope of the claims of the present invention. In the claims, the word "comprising" does not exclude other elements or steps, and the indefinite article "a" or "an" does not exclude a plurality. Any reference signs in the claims should not be construed as limiting the scope.

The invention claimed is:

1. A steam iron comprising a sole plate, said sole plate comprising a steam channel for the passage of steam, an ironing surface, vents for the passage of steam between the steam channel and the ironing surface, an aperture extending between the steam channel and the ironing surface, wherein the steam iron further comprises a fragrance cartridge received in said aperture such that it extends into the steam channel to diffuse fragrance in the steam channel, wherein the aperture secures the fragrance cartridge in the sole plate flush with the ironing surface.

2. A steam iron according to claim 1, wherein said aperture is circular with a diameter of between 5 mm-10 mm.

3. A steam iron according to claim 2, wherein the aperture comprises a screw thread adapted to cooperate with a screw thread formed in the fragrance cartridge.

4. A steam iron according to claim 1, wherein the aperture extends between the steam channel and the ironing surface in the proximity of where steam enters the steam channel.

5. A steam iron according to claim 1, comprising a fragrance receiving element and a holder to hold said fragrance receiving element.

6. A steam iron according to claim 5, wherein the fragrance receiving element extends through the holder from the steam channel to enable it to be filled with liquid fragrance without removing the holder from the aperture.

7. A steam iron according to claim 5, wherein the holder comprises a recess to receive the fragrance receiving element and wherein the recess only extends partially through the holder such that the fragrance receiving element extends partially through the holder and is inaccessible from the ironing surface when the fragrance cartridge is received in the aperture.

8. A steam iron according to claim 5, wherein the fragrance receiving element is adapted to protrude into the steam channel.

9. A steam iron according to claim 5, wherein the fragrance receiving element is made of porous material.

10. A steam iron according to claim 5, wherein the holder lies flush with the ironing surface.

11. A steam iron according to claim 5, wherein the holder is removably secured within the aperture.

12. A steam iron according to claim 11, wherein the holder is manually removable from the aperture by movement of the holder relative to the sole plate.

13. A method of imparting a fragrance to steam intended to be sprayed over garments during ironing by a steam iron having a sole plate, said sole plate comprising a steam channel for the passage of steam, an ironing surface, vents for the passage of steam between the steam channel and the ironing surface and an aperture extending between the steam channel and the ironing surface, wherein the method further comprises the steps of:

disposing a fragrance cartridge in said aperture such that it extends into the steam channel to diffuse fragrance in the steam channel and is flush with the ironing surface, passing steam into the steam channel.

* * * * *